United States Patent [19]  
Franz et al.

[11] 4,218,235
[45] Aug. 19, 1980

[54] ESTER DERIVATIVES OF N-TRIFLUOROACETYL-N-PHOSPHONOMETHYLGLYCINE AND THE HERBICIDAL USE THEREOF

[75] Inventors: John E. Franz, Crestwood; Robert J. Kaufman, University City, both of Mo.

[73] Assignee: Monsanto Company, St. Louis, Mo.

[21] Appl. No.: 922,920

[22] Filed: Jul. 10, 1978

[51] Int. Cl.$^2$ ............................ A01N 9/36; C07F 9/02
[52] U.S. Cl. .................................... 71/86; 260/941
[58] Field of Search ........................ 71/86; 260/941

[56] References Cited

U.S. PATENT DOCUMENTS

| | | | |
|---|---|---|---|
| 3,799,758 | 3/1974 | Franz | 71/86 |
| 3,819,353 | 6/1974 | Langsdorf, Jr. | 71/86 |
| 3,835,000 | 9/1974 | Frazier et al. | 71/86 |
| 3,853,530 | 12/1974 | Franz | 71/86 |
| 3,970,695 | 7/1976 | Rueppel | 71/86 |
| 4,053,505 | 10/1977 | Dutra | 260/502.5 |
| 4,089,671 | 5/1978 | Dutra | 71/86 |
| 4,108,626 | 8/1978 | McIntosh | 71/86 |

FOREIGN PATENT DOCUMENTS 849907 6/1977 Belgium ..................... 71/86

OTHER PUBLICATIONS

Rueppel et al., "Derivatization of Aminoalkylphosphonic, etc.," (1975), Biomed. Mass Spec., pp. 28-31 (1976).

Primary Examiner—Glennon H. Hollrah  
Attorney, Agent, or Firm—William T. Black; Donald W. Peterson

[57] ABSTRACT

This disclosure relates to ester derivatives of N-trifluoroacetyl-N-phosphonomethylglycine, to herbicidal compositions containing same and to the herbicidal use thereof. The ester derivatives of N-trifluoroacetyl-N-phosphonomethylglycine are useful as herbicides.

21 Claims, No Drawings

ESTER DERIVATIVES OF N-TRIFLUOROACETYL-N-PHOSPHONOMETHYLGLYCINE AND THE HERBICIDAL USE THEREOF

This invention relates to ester derivatives of N-trifluoroacetyl-N-phosphonomethylglycine, to herbicidal compositions containing same and to herbicidal methods. More particularly, this invention relates to ester derivatives of N-trifluoroacetyl-N-phosphonomethylglycine, wherein the groups bonded to the phosphorus atom are different than the group attached to the carboxyl group.

In accordance with U.S. Pat. No. 3,970,695, issued July 20, 1976, N-perfluoroacyl-N-phosphonomethylglycines of the formula

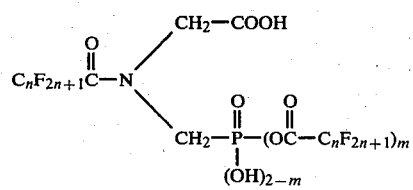

wherein n is an integer of from 1 to 4 and m is 1 or 0 are produced by reacting a perfluoroacyl anhydride with N-phosphonomethylglycine in the presence of a perfluoroalkanoic acid to form the compound of the formula wherein m is 1 and then by hydrolysis to form the compounds wherein m is 0.

N-phosphonomethylglycine, its salts, amides, esters and other derivatives are disclosed in U.S. Pat. No. 3,799,758 and are shown to be post-emergent herbicides. Other derivatives of N-phosphonomethylglycine and the plant growth regulation use thereof are disclosed in U.S. Pat. No. 3,853,530. The production of triesters of N-phosphonomethylglycine is disclosed in U.S. Pat. Nos. 4,053,505 and 3,835,000 and in Belgian Pat. No. 849,907.

Ester derivatives of N-trifluoroacetyl-N-phosphonomethylglycine wherein the ester groups attached to phosphorus and to the carboxyl group are all the same and are alkyl groups as disclosed by Rueppel et al, *Biomedical Mass Spectrometry*, Volume 3 (1976), pages 28–31. These compounds were prepared by preparing the N-trifluoroacetyl derivative of U.S. Pat. No. 3,970,695 and then reacting it with diazobutane in n-butanol.

The novel N-trifluoroacetyl-N-phosphonomethylglycine esters of this invention are those mixed ester derivatives having the formula

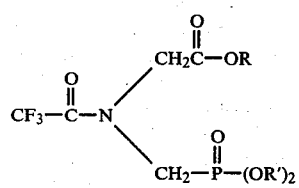

wherein R is an alkyl group containing 1 to 10 carbon atoms or a phenyl group and R' is a member of the group consisting of allyl, naphthyl, benzyl and ring-substituted benzyl wherein the substituent is halo, cyano, nitro and trifluoromethyl, phenyl and phenyl substituted with one or two groups selected from the class consisting of halo, cyano, nitro and trifluoromethyl.

As employed herein, the term "halo" includes chloro, bromo, iodo and fluoro. Preferably, the halo groups are chloro or fluoro.

Illustrative of the groups which R' represents are monosubstituted phenyl groups wherein the substituent is in the ortho, meta or para position, for example, chlorophenyl, bromophenyl, fluorophenyl, cyanophenyl, nitrophenyl and trifluorophenyl and the disubstituted phenyl groups wherein the substituents are the same or different and are located in the 2, 3, 4, 5 or 6 positions of the phenyl group, for example, dichlorophenyl, dibromophenyl, chlorocyanophenyl, dicyanophenyl, dinitrophenyl, bromonitrophenyl, chlorotrifluoromethylphenyl and the like. The ring-substituted benzyl groups include benzyl groups containing the substituents set forth above for the substituted phenyl groups.

Illustrative of the alkyl groups represented by R are, for example, methyl, ethyl, propyl, hexyl, cyclohexyl, decyl and their isomers. Preferably, R is a lower alkyl group, i.e., an alkyl group containing from 1 to 4 carbon atoms.

The novel compounds of this invention are produced by reacting an ester dichloride of N-trifluoroacetyl-N-phosphonomethylglycine having the formula

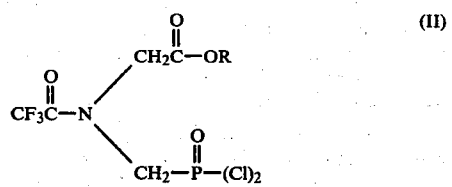

wherein R is as above-defined with a hydroxy compound having the formula

R'—O—H wherein R' is as above-defined in an organic solvent and in the presence of a tertiary amine hydrogen chloride acceptor under essentially anhydrous conditions at a temperature of from about 10° C. to about 50° C. preferably at ambient temperatures.

In producing the compounds of this invention by the above reaction, the tertiary amine hydrogen chloride acceptor is preferably used in excess of stoichiometric to insure completeness of reaction. By the term "tertiary amine hydrogen chloride acceptor" as employed herein is meant tertiary alkylamines such as trimethylamine, triethylamine, tributylamine, trihexylamine and the like as well as aromatic tertiary amines such as pyridine, quinoline and the like.

The ratio of the reactants can vary over wide ranges. It is, of course, apparent to those skilled in the art that each chlorine atom in the N-trifluoroacetyl-N-phosphonomethylglycinyl dichloride will react with one alcohol group (R'—O—H) and that, therefore, one would employ the reactants in equivalent amounts. When employing an alcohol which is volatile, it is sometimes desirable to employ an excess of the alcohol. In other instances such with the phenols, it is sometimes preferred to use a slight excess of the glycinyl dichloride for ease of recovery of the product.

The ester dichlorides of Formula II employed as a reactant in producing the compounds of this invention are prepared by reacting an ester of N-phosphonomethylglycine of the formula

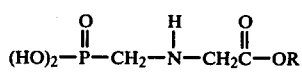

wherein R has the above defined meaning with trifluoroacetic acid anhydride at temperatures of from about 10° C. to about 35° C., removing any excess anhydride and then treating the reaction product with excess thionyl chloride under refluxing conditions. The excess thionyl chloride is removed under vacuum to yield the dichlorides of Formula II.

The compounds of this invention are useful as herbicides.

The following non-limiting examples will serve to demonstrate to those skilled in the art the manner in which specific compounds within the scope of this invention can be prepared.

EXAMPLE 1

A solution of N-trifluoroacetyl-N-(dichlorophosphonomethyl)glycinyl chloride (1.6 g, 0.005 mole) in ether (20 ml.) was added dropwise to a stirred solution of phenol (1.6 g, 0.017 mole) and triethylamine (1.72 g, 0.017 mole) in 40 ml. of ether. The mixture was stirred for 1 hour at 20° C., then filtered. The filtrate was concentrated in vacuo to an orange oil which was extracted into boiling petroleum ehter. Concentration of the petroleum ether extract afforded phenyl N-trifluoroacetyl-N-(diphenoxyphosphonomethyl)glycinate (2.3 g) as a yellow oil. An analytical sample was obtained by chromatography on florasil which yielded phenyl N-trifluoroacetyl-N-(diphenoxyphosphonomethyl)glycinate as a solid, m.p. 166°-174° C. with decomposition.

Anal. Calc'd: C, 55.99; H, 3.88; N, 2.84; F, 11.55.
Found: C, 56.23; H, 4.01; N, 2.92; F, 11.81.

EXAMPLE 2

A solution of ethyl N-trifluoroacetyl-N-(dichlorophosphonomethyl)glycinate (1.65 g, 0.005 mole) in 20 ml. of ether was added dropwise to a solution of phenol (0.95 g, 0.010 mole) and triethylamine (1.05 g, 0.010 mole) in 30 ml. of ether. The reaction mixture was stirred for one hour, then filtered. Concentration of the filtrate in vacuo afforded an oil which was extracted into boiling petroleum ether. Concentration of the petroleum ether extract afforded ethyl N-trifluoroacetyl-N-(diphenoxyphosphonomethyl)glycinate (2.2 g) as a very light yellow solid which crystallized on standing, m.p. 59.5°-63.5° C.

Anal. Calc'd: C, 51.24; H, 4.30; N, 3.15; F, 12.80.
Found: C, 51.36; H, 4.22; N, 3.11; F, 12.72.

EXAMPLE 3

To a solution of p-nitrobenzyl alcohol (3.98 g, 0.026 mole) and triethylamine (2.63 g, 0.026 mole) in 150 ml. of dry ether was added ethyl N-trifluoroacetyl-N-(dichlorophosphonomethyl)glycinate (4.29 g, 0.013 mole) in ether (60 ml.). The resulting mixture was stirred for 16 hours at room temperature, then tetrahydrofuran (200 ml.) was added and the mixture filtered. The filtrate was concentrated in vacuo to give 4.05 g of a white solid, which was recrystallized from isopropanol to afford ethyl N-trifluoroacetyl-N-(bis(p-nitrobenzyloxy)phosphonomethyl)glycinate (2.6 g), m.p. 97°-99° C.

Anal. Calc'd: C, 44.77; H, 3.76; N, 7.46; P, 5.50.
Found: C, 44.69; H, 3.72; N, 7.35; P, 5.35.

EXAMPLE 4

To a solution of ethyl N-trifluoroacetyl-N-(dichlorophosphonomethyl)glycinate (3.3 g, 0.01 mole) in 100 ml. of ether was added a solution of 2-naphthol (2.88 g, 0.02 mole) and triethylamine (2.02 g, 0.02 mole) in ether (75 ml.). The resulting mixture was stirred at 20° C. for 4 hours, then filtered. The filtrate was concentrated in vacuo to give ethyl N-trifluoroacetyl-N-(dinaphthyloxyphosphonomethyl)glycinate as a light yellow gum (2.55 g).

Anal. Calc'd: C, 59.45; H, 4.25; N, 2.57; P, 5.68.
Found: C, 59.71; H, 4.38; N, 2.54; P, 5.65.

EXAMPLE 5

A solution of ethyl N-trifluoroacetyl-N-(dichlorophosphonomethyl)glycinate (4.95 g, 0.015 mole) in dry ether (150 ml.) was added dropwise with good agitation to a solution of m-chlorophenol (3.9 g, 0.03 mole) and triethylamine (3.03 g, 0.03 mole) in dry ether (75 ml.). The reaction was stirred at room temperature for 48 hours, then filtered to remove triethylamine hydrochloride. The filtrate was concentrated in vacuo and the residue was extracted into warm petroleum ether. The petroleum ether solution was concentrated in vacuo to afford ethyl N-trifluoroacetyl-N-(bis(m-chlorophenoxy)phosphonomethyl)glycinate as a light yellow oil. Short path distillation at 50°/0.5 mm. removed a small amount of unreacted phenol and afforded pure ethyl N-trifluoroacetyl-N-(bis(m-chlorophenoxy)phosphonomethyl)glycinate, $N_D^{22}=1.5178$.

Anal. Calc'd: C, 44.38; H, 3.33; N, 2.72; P, 6.02.
Found: C, 44.34; H, 3.35; N, 2.73; P, 5.92.

EXAMPLE 6

A solution of ethyl N-trifluoroacetyl-N-(dichlorophosphonomethyl)glycinate (4.95 g, 0.015 mole) in ether (100 ml.) was added dropwise with good agitation to a solution of m-cyanophenol (3.57 g, 0.03 mole) and triethylamine (3.03 g, 0.03 mole) in dry ether (50 ml.). The reaction mixture was stirred at room temperature for several hours, then filtered. The filtrate was washed with a 5% solution sodium hydroxide, dried over magnesium sulfate, and concentrated in vacuo to afford ethyl N-trifluoroacetyl-N-(bis(m-cyanophenoxy)phosphonomethyl)glycinate (3.4 g.) as a yellow gum, $N_D^{22}=1.5185$.

Anal. Calc'd: C, 50.92; H, 3.46; N, 8.48; P, 6.25.
Found: C, 51.15; H, 3.67; N, 8.41; P, 6.08.

EXAMPLE 7

A solution of ethyl N-trifluoroacetyl-N-dichlorophosphonomethyl)glycinate (3.3 g, 0.01 mole) in dry ether (100 ml.) was added dropwise to a solution of m-trifluoromethylphenol (3.25 g, 0.02 mole) and triethylamine (2.02 g, 0.02 mole) in ether (50 ml.). The solution as stirred overnight at room temperature, then filtered. The filtrate was washed with 5% sodium hydroxide solution, dried over magnesium sulfate and concentrated to yield ethyl N-trifluoroacetyl-N-(bis(m-trifluoromethylphenoxy)phosphonomethyl)glycinate as an oil, (2.1 g), $N_D^{22}=1.4584$.

EXAMPLE 8

A solution of ethyl N-trifluoroacetyl-N-(dichlorophosphonomethyl)glycinate (5.28 g, 0.016 mole) in dry ether (80 ml.) was added to a solution of m-nitrophenol (4.45 g, 0.032 mole) and triethylamine (3.23 g, 0.032 mole) in dry ether (100 ml.). The resulting mixture was stirred for 2.5 hours, then filtered and the filtrate was concentrated in vacuo. The residual oil was taken up in ether and precipitated with petroleum ether to afford ethyl N-trifluoroacetyl-N-(bis(m-nitrophenoxy)phosphonomethyl)glycinate as a glass (8.5 g), $N_D^{26.6} = 1.5278$.

Anal. Calc'd: C, 42.63; H, 3.20; N, 7.85; P, 5.79. Found: C, 42.49; H, 3.38; N, 7.83; P, 5.71.

EXAMPLE 9

To a solution of m-chlorobenzyl alcohol (2.7 g, 0.019 mole) and triethylamine (1.9 g, 0.019 mole) in tetrahydrofuran (50 ml.) was added ethyl N-trifluoroacetyl-N-(dichlorophosphonomethyl)glycinate (3.13 g, 0.0095 mole) in tetrahydrofuran (25 ml.). The resulting mixture was stirred at 20° C. for 3 hours, then filtered. The filtrate was concentrated in vacuo to afford 5.2 g of yellow oil. This oil was chromatographed on silica gel eluting first with benzene, then with ethyl ether to afford 3.7 g of pure ethyl N-trifluoroacetyl-N-(bis(m-chlorobenzyloxy)phosphonomethyl)glycinate, $N_D^{26.6} = 1.5181$.

Anal. Calc'd: C, 46.51; H, 3.84; N, 2.58; P, 5.71. Found: C, 46.36; H, 3.90; N, 2.68; P, 5.65.

EXAMPLE 10

To a solution of ethyl N-trifluoroacetyl-N-(dichlorophosphonomethyl)glycinate (6.6 g, 0.02 mole) in ether (200 ml.) was added a solution of allyl alcohol (2.32 g, 0.04 mole) and triethylamine (4.04 g, 0.04 mole) in ether (75 ml.). The resulting mixture was stirred for 5 days at 20° C. The mixture was filtered and the filtrate was concentrated in vacuo to afford a clear oil. This oil was extracted into petroleum ether, then concentrated in vacuo to give 6.25 g of ethyl N-trifluoroacetyl-N-(diallyloxyphosphonomethyl)glycinate as an oil, $N_D^{26.6} = 1.4382$.

Anal. Calc'd: C, 41.83; H, 5.13; N, 3.75; P, 8.30. Found: C, 41.61; H, 5.28; N, 4.00; P, 8.09.

EXAMPLE 11

A solution of n-decyl N-trifluoroacetyl-N-dichlorophosphonomethyl)glycinate (4.42 g, 0.01 mole) in ether (100 ml.) was treated with a solution of 2,4-dichlorophenol (3.26 g, 0.02 mole) and triethylamine (2.02 g, 0.02 mole) in ether (50 ml.). The resulting mixture was stirred overnight, then filtered. The filtrate was concentrated in vacuo to afford 6.9 g of n-decyl N-trifluoroacetyl-N-(bis(2,4-dichlorophenoxy)phosphonomethyl)-glycinate as a yellow gum, $N_D^{26.6} = 1.5083$.

Anal. Calc'd: C, 46.64; H, 4.49; N, 2.01. Found: C, 46.54; N, 4.75; N, 2.21.

EXAMPLE 12

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the four-week observations are omitted.

The post-emergence herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | | | |
| --- | --- | --- | --- |
| A | Canada Thistle* | K | Barnyardgrass |
| B | Cocklebur | L | Soybean |
| C | Velvetleaf | M | Sugar Beet |
| D | Morningglory | N | Wheat |
| E | Lambsquarters | O | Rice |
| F | Smartweed | P | Sorghum |
| G | Yellow Nutsedge* | Q | Wild Buckwheat |
| H | Quackgrass* | R | Hemp Sesbania |
| I | Johnsongrass* | S | Panicum Spp |
| J | Downy Brome | T | Crabgrass |

*Established from vegetative propagules.

Table I

| Compound of Example No. | WAT | kg h | A | B | C | D | E | F | G | H | I | J | K |
| --- | --- | --- | --- | --- | --- | --- | --- | --- | --- | --- | --- | --- | --- |
| 1 | 4 | 11.2 | 1 | — | 1 | 2 | 3 | 1 | 2 | 3 | 3 | 1 | 3 |
| 1 | 4 | 4.48 | 1 | — | 1 | 2 | 2 | 0 | 1 | 1 | 1 | 0 | 2 |
| 2 | 4 | 11.2 | 3 | — | 4 | 4 | 4 | 2 | 4 | 3 | 4 | 4 |
| 2 | 4 | 4.48 | 2 | — | 2 | 3 | 4 | 3 | 2 | 2 | 3 | 2 | 3 |
| 3 | 4 | 11.2 | 2 | 2 | 1 | 0 | 0 | 0 | 1 | 0 | 1 | 1 | 1 |

Table I-continued

| Compound of Example No. | WAT | kg/h | A | B | C | D | E | F | G | H | I | J | K |
|---|---|---|---|---|---|---|---|---|---|---|---|---|---|
| 4 | 4 | 11.2 | 1 | 0 | 1 | 1 | 1 | 0 | 1 | 1 | 0 | 1 | 2 |
| 5 | 4 | 11.2 | 1 | 3 | 3 | 3 | 3 | 4 | 2 | 4 | 2 | 2 | 4 |
| 5 | 4 | 5.6 | 1 | 3 | 2 | 2 | 3 | 3 | 2 | 3 | 1 | 1 | 3 |
| 6 | 4 | 11.2 | 1 | 3 | 2 | 3 | 4 | 1 | 2 | 2 | 2 | 2 | 3 |
| 6 | 4 | 5.6 | 1 | 3 | 2 | 3 | 3 | 2 | 2 | 2 | 2 | 2 | 4 |
| 7 | 4 | 11.2 | 1 | 3 | 2 | 2 | 4 | 0 | 2 | 1 | 1 | 1 | 3 |
| 7 | 4 | 5.6 | 1 | 2 | 1 | 2 | 4 | 1 | 1 | 1 | 0 | 1 | 3 |
| 8 | 4 | 11.2 | 3 | 3 | 1 | 3 | 4 | 1 | 3 | 3 | 4 | 2 | 3 |
| 8 | 4 | 5.6 | 1 | 2 | 1 | 2 | 4 | 4 | 3 | 3 | 3 | 4 | |
| 9 | 4 | 11.2 | 0 | 1 | 0 | 0 | 0 | 0 | 0 | 0 | 0 | 0 | 2 |
| 10 | 4 | 11.2 | 4 | 1 | 1 | 1 | 4 | 2 | 2 | 2 | 2 | 1 | 2 |
| 10 | 2 | 5.6 | 1 | 0 | 0 | 0 | 1 | 0 | 0 | 0 | 0 | 0 | 1 |
| 11 | 2 | 11.2 | 0 | 0 | 0 | 0 | — | 1 | 0 | 0 | 0 | 0 | 0 |

Table II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 1 | 4 | 4.48 | 2 | 1 | 2 | 1 | 3 | 2 | 0 | 2 | 0 | 2 | 2 | 1 | 3 | 3 | 2 | 3 |
| 2 | 4 | 4.48 | 3 | 3 | 2 | 2 | 3 | — | 1 | 3 | 2 | 2 | 2 | 2 | 3 | 4 | 3 | 3 |
| 2 | 4 | 1.12 | 1 | 0 | 2 | 1 | 2 | 2 | 0 | 2 | 1 | 1 | 1 | 2 | 2 | 2 | 2 | 3 |
| 2 | 4 | .224 | 1 | 0 | 1 | 0 | 0 | 1 | 0 | 2 | 0 | 1 | 0 | 0 | 0 | 0 | 0 | 2 |
| 5 | 4 | 5.6 | 2 | 1 | 2 | 2 | 2 | 2 | 1 | 2 | 3 | 4 | 2 | — | 1 | 3 | 3 | 3 |
| 5 | 4 | 1.12 | 1 | 1 | 1 | 1 | 1 | 1 | 0 | 1 | 2 | 2 | 1 | — | 0 | 2 | 2 | 3 |
| 6 | 4 | 5.6 | 3 | 1 | 3 | 3 | 2 | 3 | 1 | 3 | 2 | 4 | 3 | 2 | 2 | 4 | 4 | 4 |
| 6 | 4 | 1.12 | 1 | 2 | 1 | 1 | 2 | 2 | 1 | 2 | 4 | 1 | 3 | 1 | 3 | 3 | 3 | 3 |
| 7 | 4 | 5.6 | 3 | 1 | 2 | 1 | 2 | 2 | 0 | 1 | 3 | 1 | 0 | 1 | 2 | 1 | 2 | 2 |
| 8 | 4 | 5.6 | 3 | 4 | 4 | 4 | 4 | 3 | 2 | 2 | 2 | 4 | 2 | 3 | 4 | 4 | 3 | 4 |
| 8 | 4 | 1.12 | 1 | 1 | 2 | 2 | 2 | 2 | 0 | 1 | 1 | 1 | 2 | 1 | 1 | 1 | 1 | 4 |
| 10 | 2 | 5.6 | 1 | 0 | 1 | 0 | 0 | 1 | 0 | 1 | 0 | 1 | 1 | 0 | 0 | 0 | 0 | 1 |
| 10 | 2 | 1.12 | 1 | 1 | 0 | 0 | 0 | 0 | 0 | 0 | 0 | 1 | 0 | 0 | 0 | 0 | 0 | 1 |

EXAMPLE 13

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegatative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in the following table.

The pre-emergent herbicidal activity index used below is based upon average percent control of each species as follows:

| Percent Control | Index |
|---|---|
| 0-24% control | 0 |
| 25-49% control | 1 |
| 50-74% control | 2 |
| 75%-100% control | 3 |

Plant species in the table are identified by the same code letters used in the previous example.

Table III

| Compound of Example No. | WAT | kg/h | A | B | C | D | E | F | G | H | I | J | K |
|---|---|---|---|---|---|---|---|---|---|---|---|---|---|
| 2 | 4 | 11.2 | 3 | 0 | 0 | 1 | 3 | 0 | 0 | 1 | 0 | 1 | 0 |
| 3 | 2 | 11.2 | 0 | 0 | 0 | 0 | 3 | 0 | 0 | 0 | 0 | 0 | 0 |
| 5 | 2 | 11.2 | 3 | 0 | 0 | 0 | 0 | 0 | 1 | 1 | 1 | 0 | 0 |
| 6 | 2 | 11.2 | 3 | 0 | 0 | 0 | 0 | 0 | 0 | 1 | 0 | 0 | 0 |
| 7 | 2 | 11.2 | 3 | 0 | 0 | 0 | 0 | 0 | 1 | 0 | 1 | 0 | 0 |
| 8 | 2 | 11.2 | | | | | | | | | | | |
| | 0 | 0 | 0 | 0 | 0 | 1 | 1 | 0 | 0 | 0 | | | |
| 11 | 2 | 11.2 | 1 | 0 | 0 | 0 | 0 | 0 | 0 | 0 | 0 | 1 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compound or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compound or compositions of this invention to the plant is essential and critical for the practice of the present invention. The exact amount of active ingredient to be employed is dependent upon the response desired in the plant as well as such other factors at the plant species and stage of development thereof, and the amount of rainfall as well as the specific glycine employed. In foliar treatment for the control of vegetative growth, the active ingredients are applied in amounts from about 0.112 to about 22.4 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

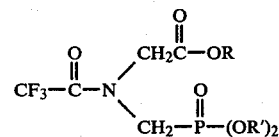

wherein R is an alkyl group containing from 1 to 10 carbon atoms or a phenyl group and R' is a member of the group consisting of allyl, naphthyl, benzyl and ring-substituted benzyl wherein the substituent is halo, cyano, nitro or trifluoromethyl, phenyl and phenyl containing one or two groups selected from the class consisting of halo, cyano, nitro and trifluoromethyl.

2. A compound of claim 1 wherein R' is phenyl or phenyl substituted with one or two groups selected from the group consisting of halo, cyano, nitro and trifluoromethyl.

3. A compound of claim 2 wherein R is a lower alkyl group.

4. A compound of claim 1 wherein R is a lower alkyl group and R' is a naphthyl group.

5. A compound of claim 3 which is ethyl N-trifluoroacetyl-N-(diphenoxyphosphonomethyl)glycinate.

6. A compound of claim 3 which is ethyl N-trifluoroacetyl-N-(bis(m-nitrophenoxy)phosphonomethyl)glycinate.

7. A compound of claim 4 which is ethyl N-trifluoroacetyl-N-(dinaphthyloxyphosphonomethyl)-glycinate.

8. A herbicidal composition comprising an inert adjuvant and a herbicidally effective amount of a compound of the formula

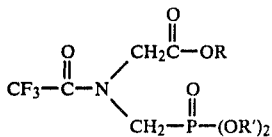

wherein R is an alkyl group containing from 1 to 10 carbon atoms or a phenyl group and R' is a member of the group consisting of allyl, naphthyl, benzyl and ring-substituted benzyl wherein the substituent is halo, cyano, nitro or trifluoromethyl, phenyl and phenyl containing one or two groups selected from the class consisting of halo, cyano, nitro and trifluoromethyl.

9. A herbicidal composition of claim 8 wherein R' is phenyl or phenyl substituted with one or two groups selected from the group consisting of halo, cyano, nitro and trifluoromethyl.

10. A herbicidal composition of claim 9 wherein R is a lower alkyl group.

11. A herbicidal composition of claim 8 wherein R is a lower alkyl group and R' is a naphthyl group.

12. A herbicidal composition of claim 9 wherein the compound is ethyl N-trifluoroacetyl-N-(diphenoxyphosphonomethyl)glycinate.

13. A herbicidal composition of claim 9 wherein the compound is ethyl N-trifluoroacetyl-N-(bis(m-nitrophenoxy)phosphonomethyl)glycinate.

14. A herbicidal composition of claim 11 wherein the compound is ethyl N-trifluoroacetyl-N-(dinaphthyloxyphosphonomethyl)glycinate.

15. A herbicidal method which comprises contacting the plant or plant growth medium with a herbicidally effective amount of a compound of the formula

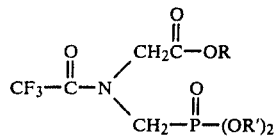

wherein R is an alkyl group containing from 1 to 10 carbon atoms or a phenyl group and R' is a member of the group consisting of allyl, naphthyl, benzyl and ring-substituted benzyl wherein the substituent is halo, cyano, nitro or trifluoromethyl, phenyl and phenyl containing one or two groups selected from the class consisting of halo, cyano, nitro and trifluoromethyl.

16. A herbicidal method of claim 15 wherein R' is phenyl or phenyl substituted with one or two groups selected from the group consisting of halo, cyano, nitro and trifluoromethyl.

17. A herbicidal method of claim 16 wherein R is a lower alkyl group.

18. A herbicidal method of claim 15 wherein R is a lower alkyl group and R' is a naphthyl group.

19. A herbicidal method of claim 17 wherein the compound is ethyl N-trifluoroacetyl-N-(diphenoxyphosphonomethyl)glycinate.

20. A herbicidal method of claim 17 wherein the compound is ethyl N-trifluoroacetyl-N-(bis(m-nitrophenoxy)phosphonomethyl)glycinate.

21. A herbicidal method of claim 18 wherein the compound is ethyl N-trifluoroacetyl-N-(dinaphthyloxyphosphonomethyl)glycinate.

* * * * *